(12) United States Patent
Sasaki

(10) Patent No.: US 8,597,181 B1
(45) Date of Patent: Dec. 3, 2013

(54) TRANSPARENT SURGICAL PELVIC RETRACTOR

(76) Inventor: Larry Sasaki, Shreveport, LA (US)

( * ) Notice: Subject to any disclaimer, the term of this patent is extended or adjusted under 35 U.S.C. 154(b) by 223 days.

(21) Appl. No.: 12/802,309

(22) Filed: Jun. 3, 2010

Related U.S. Application Data

(60) Provisional application No. 61/217,704, filed on Jun. 3, 2009.

(51) Int. Cl.
*A61B 1/32* (2006.01)

(52) U.S. Cl.
USPC .......................................... 600/208; 600/201

(58) Field of Classification Search
USPC ..................... 600/201–219, 227–237; 606/90
See application file for complete search history.

(56) References Cited

U.S. PATENT DOCUMENTS

| 3,807,393 | A | * | 4/1974 | McDonald | 600/208 |
| 4,984,564 | A | * | 1/1991 | Yuen | 600/207 |
| 5,433,190 | A | * | 7/1995 | Sunalp | 600/236 |
| 5,454,365 | A | * | 10/1995 | Bonutti | 600/204 |
| 5,456,246 | A | * | 10/1995 | Schmieding et al. | 600/201 |
| 5,716,329 | A | * | 2/1998 | Dieter | 600/210 |
| 5,902,315 | A | * | 5/1999 | DuBois | 606/190 |
| 5,906,577 | A | * | 5/1999 | Beane et al. | 600/207 |
| 2008/0077156 | A1 | * | 3/2008 | Emstad | 606/105 |

* cited by examiner

*Primary Examiner* — Eduardo C Robert
*Assistant Examiner* — James Palmer
(74) *Attorney, Agent, or Firm* — R. Keith Harrison

(57) ABSTRACT

A transparent surgical pelvic retractor includes a transparent, generally semicircular retractor body having a retractor interior; a concave inner surface facing the retractor interior; and a convex outer surface opposite the inner surface. A surgical retractor method is also disclosed.

9 Claims, 9 Drawing Sheets

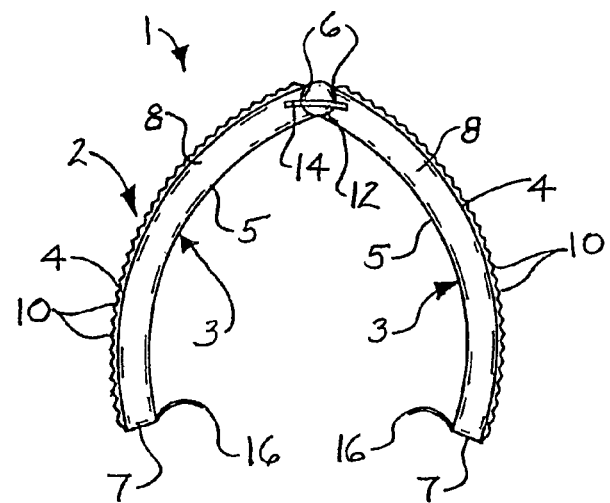
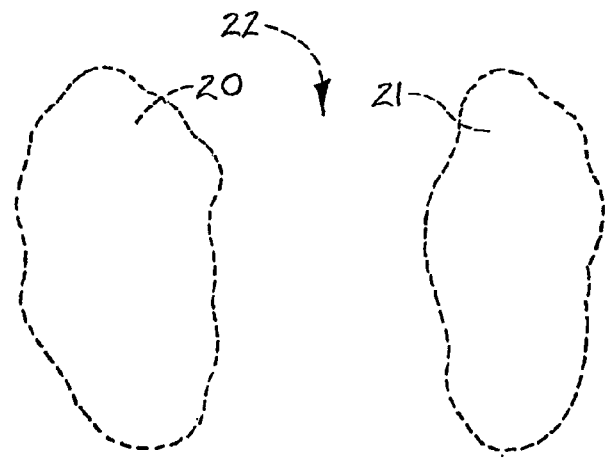
FIG. 4
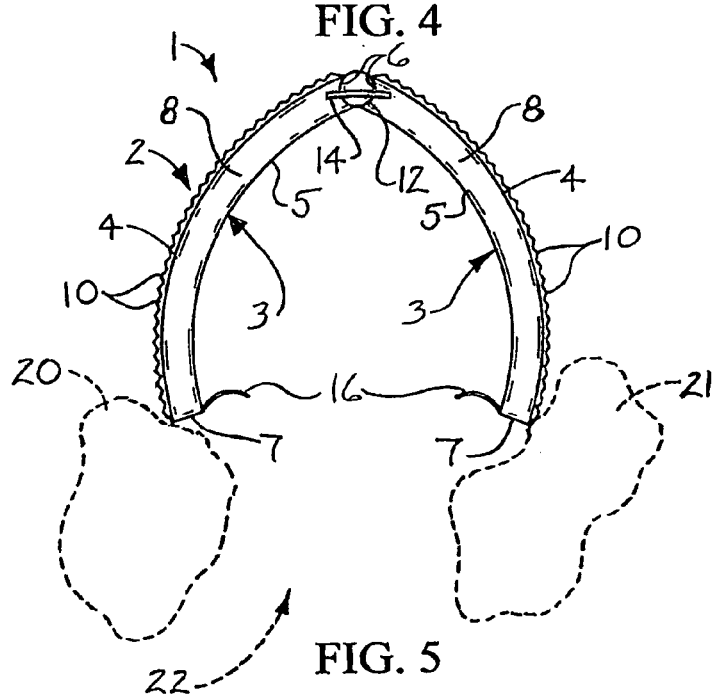
FIG. 5

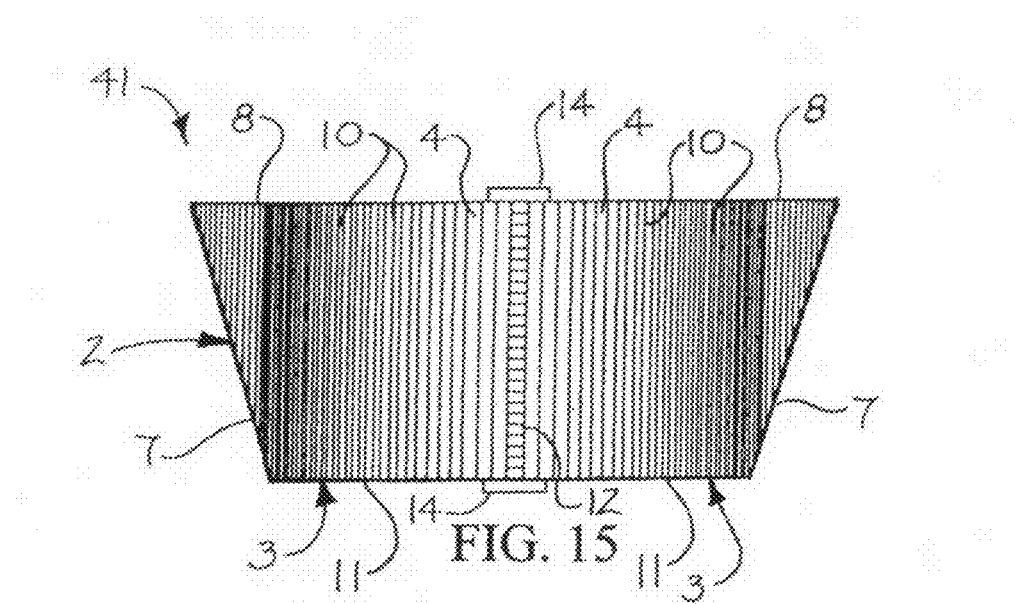
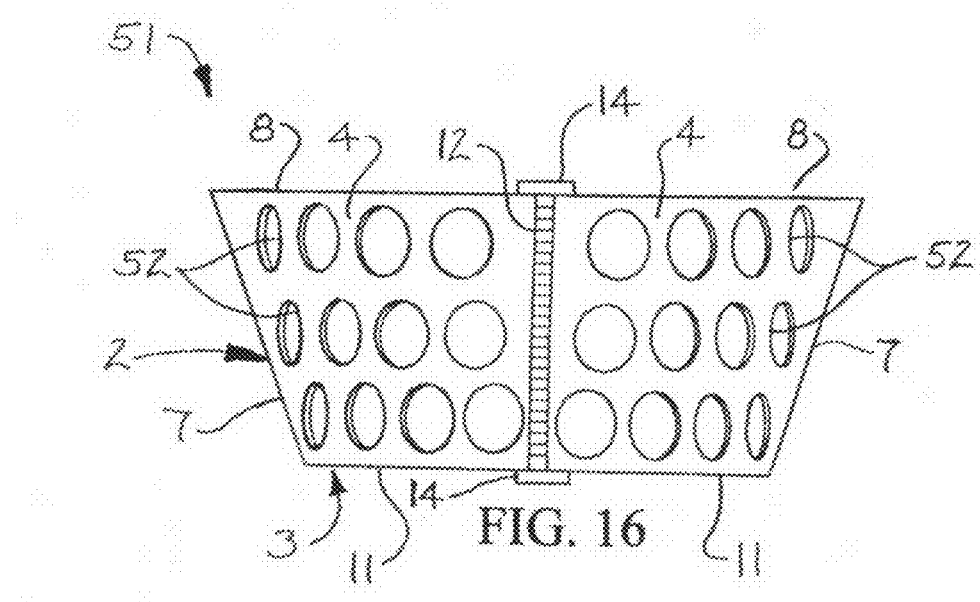

TRANSPARENT SURGICAL PELVIC RETRACTOR

CROSS-REFERENCE TO RELATED APPLICATIONS

This application claims the benefit of and incorporates by reference in its entirety U.S. Provisional Application No. 61/217,704, filed Jun. 3, 2009 and entitled "TRANSPARENT SURGICAL PELVIC RETRACTOR".

TECHNICAL FIELD

The present disclosure relates to surgical retractors. More particularly, the present disclosure relates to a transparent surgical pelvic retractor which retracts body tissues in a patient while facilitating full view of a surgical field during open surgical procedures.

BACKGROUND

In open and minimally-invasive surgical procedures, it may frequently be necessary to retract body tissues in a patient away from each other in order to maintain clarity of the surgical field. Mechanical retractors are commonly used to retract body tissues during surgical procedures. However, due to their position, conventional retractors may hinder full viewing of and access to the surgical field.

Accordingly, a transparent surgical pelvic retractor is needed which is suitable for retracting body tissues in a patient while facilitating full view of a surgical field during open and minimally-invasive surgical procedures.

SUMMARY

The present disclosure is generally directed to a transparent surgical pelvic retractor which is suitable for retracting body tissues in a patient while facilitating full view of a surgical field and of surgical instruments during implementation of open surgical procedures, particularly in the pelvis. An illustrative embodiment of the transparent surgical pelvic retractor includes a transparent, generally semicircular retractor body having a retractor interior; a concave inner surface facing the retractor interior; and a convex outer surface opposite the inner surface. The retractor body can be expanded outwardly against body tissues in a patient to enlarge the surgical field and facilitates full viewing of the surgical field and of instruments which are used in implementation of a surgical procedure. In pelvic surgical procedures, particularly rectal procedures, the retractor may be used to retract tissues such as the bladder, uterus\ and, perirectal tissues as well as gynecological and urological tissues.

The present disclosure is further generally directed to a surgical retractor method including providing a transparent surgical pelvic retractor having a retractor interior, collapsing the surgical retractor, positioning the surgical retractor between body tissues in a patient preparatory to an open surgical procedure, enlarging a surgical field in the patient by expansion of the surgical retractor against the body tissues, performing a surgical procedure by extending at least one surgical instrument through the retractor interior of the retractor into the surgical field, viewing the surgical instrument or instruments through the surgical retractor throughout the surgical procedure and removing the retractor from between the body tissues at the conclusion of the surgical procedure.

BRIEF DESCRIPTION OF THE DRAWINGS

The disclosure will now be made, by way of example, with reference to the accompanying drawings, in which:

FIG. 4 is an end view of an illustrative embodiment of the transparent surgical pelvic retractor in the collapsed configuration, preparatory to insertion of the retractor between body tissues (shown in phantom) to enlarge a surgical field;

FIG. 5 is an end view of an illustrative embodiment of the transparent surgical pelvic retractor disposed in the collapsed configuration as the retractor is inserted between the body tissues;

FIG. 15 is a top view of an alternative illustrative embodiment of the transparent surgical regractor with tapered lateral edges;

FIG. 16 is a top view of another alternative illustrative embodiment of the transparent surgical pelvic retractor with tapered lateral edges and multiple retractor body openings;

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to implement the disclosure and are not intended to limit the scope of the claims. Furthermore, there is no intention to be bound by any expressed or implied theory presented in the preceding technical field, background, brief summary or the following detailed description.

Figure 1:
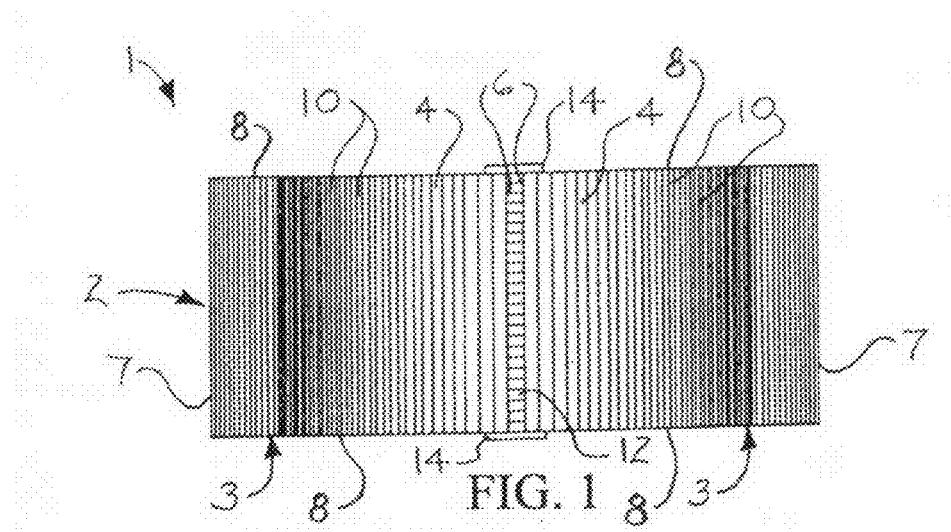
FIG. 1 is a top view of an illustrative embodiment of the transparent surgical pelvic retractor.
Figure 2:
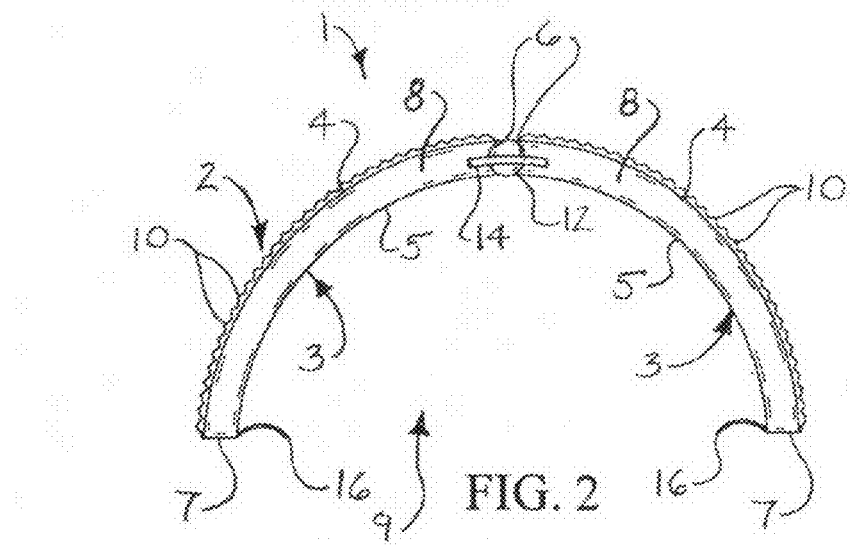
FIG. 2 is an end view of an illustrative embodiment of the transparent surgical pelvic retractor, disposed in an expanded configuration.
Figure 3:
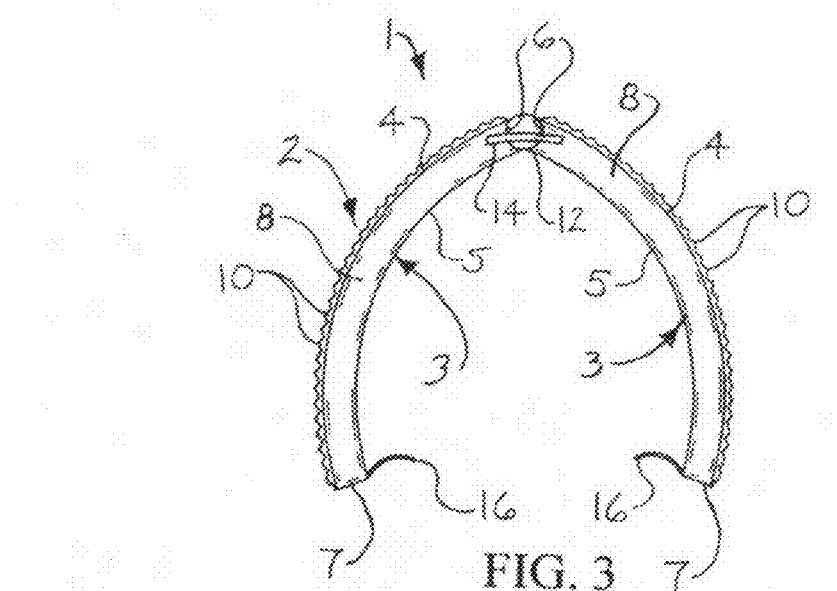
FIG. 3 is an end view of an illustrative embodiment of the transparent surgical pelvic retractor, disposed in a collapsed configuration.

Referring initially to FIGS. 1-3 of the drawings, an illustrative embodiment of the transparent surgical pelvic retractor, hereinafter retractor, is generally indicated by reference numeral 1. The retractor 1 includes a retractor body 2 which in some embodiments may have a generally rectangular configuration in top view, as illustrated in FIG. 1, and a generally semicircular configuration in end view, as illustrated in FIG. 2. In some embodiments, the retractor body 2 may include a pair of curved retractor sections 3 which are pivotally attached to each other at a hinge 12 that extends between the retractor sections 3. As illustrated in FIG. 2, the retractor sections 3 together define a retractor interior 9.

Each of the retractor sections 3 may be a transparent plastic material. Each retractor section 3 may include a generally convex outer section surface 4 and a generally concave inner section surface 5. Multiple grip ridges 10 may be provided on the outer section surface 4. As further illustrated in FIG. 2, each retractor section 3 may additionally include a medial edge 6 and a lateral edge 7 which is opposite the medial edge 6. When the surgical retractor 1 is disposed in the expanded configuration illustrated in FIG. 2, a plane of the lateral edge 7 may be oriented in generally perpendicular relationship with respect to a plane of the medial edge 6 of each retractor section 3. As illustrated in FIG. 1, each retractor section 3 may further include opposite end edges 8 which are generally parallel with respect to each other and generally perpendicular with respect to the medial edge 6 and the lateral edge 7.

The hinge 12 may pivotally attach the medial edges 6 of the retractor sections 3 to each other. Accordingly, the retractor sections 3 are capable of being pivoted between the expanded position illustrated in FIG. 2 and the collapsed configuration illustrated in FIG. 3 for purposes which will be hereinafter described. A releasable locking mechanism 14 may be provided at the hinge 12 and engage the retractor sections 3 to facilitate locking of the retractor sections 3 at a selected position with respect to each other between the collapsed configuration of FIG. 3 and the expanded configuration of FIG. 2, according to the knowledge of those skilled in the art. As illustrated in FIGS. 2 and 3, in some embodiments a finger grip 16 may be provided at the lateral edge 7 of each retractor section 3 and may extend into the retractor interior 9 for purposes which will be hereinafter described. Each finger grip 16 may be generally curved in end view, as illustrated in FIGS. 2 and 3.

Referring next to FIGS. 4-7 of the drawings, in typical application the retractor 1 may be used to retract a first body tissue 20 and a second body tissue 21 away from each other in a surgical patient (not illustrated) to implement an open or minimally-invasive surgical procedure which is carried out in a surgical field 22 between the first body tissue 20 and the second body tissue 21. In some applications, the first body tissue 20 and the second body tissue 21 may be body tissues such as the bladder, uterus, perirectal tissues, gynecological tissues or urological tissues, for example and without limitation, in the pelvic region of the patient. Accordingly, the retractor sections 3 of the retractor body 2 may initially be pivoted inwardly toward each other on the hinge 12 to fold the retractor sections 3 from the expanded configuration illustrated in FIG. 2 to the collapsed configuration illustrated in FIG. 3. The retractor sections 3 may be pivoted on the hinge 12 and collapsed inwardly by applying inward finger pressure on the finger grips 16 with one hand as the retractor body 2 is gripped at the grip ridges 10 with the other hand.

Figure 6:
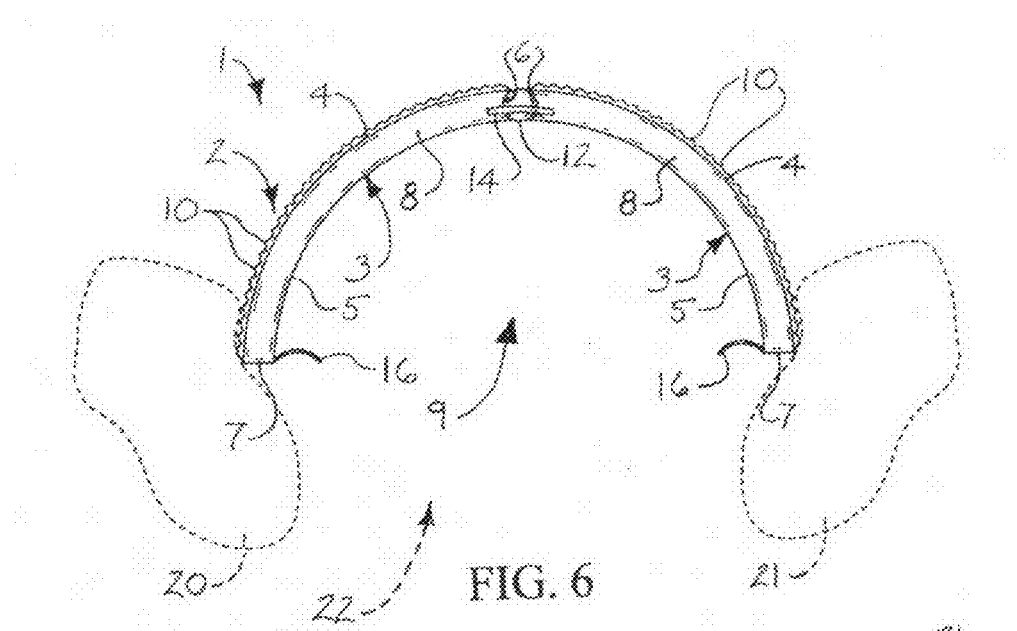
FIG. 6 is an end view of an illustrative embodiment of the transparent surgical pelvic retractor after the retractor is inserted between the body tissues and expanded to separate the tissues and enlarge the surgical field.
Figure 7:
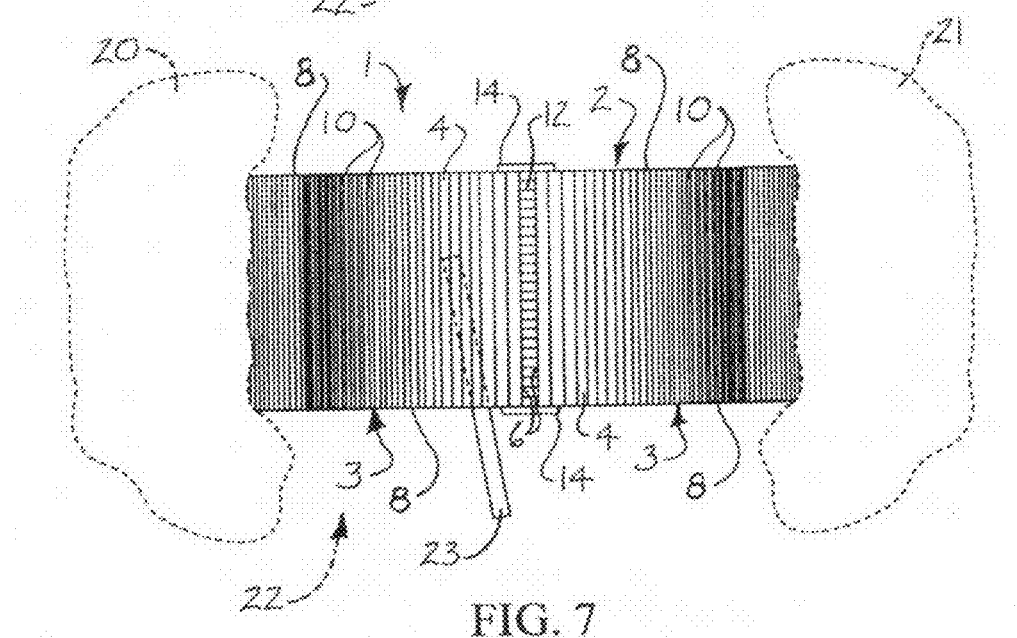
FIG. 7 is a top view of an illustrative embodiment of the transparent surgical pelvic retractor, expanded between the body tissues to define the surgical field and more particularly illustrating insertion of a surgical instrument into the surgical field beneath the retractor and viewing of the surgical instrument through the retractor.

As illustrated in FIGS. 4 and 5, the collapsed retractor body 2 is next extended between the first body tissue 20 and the second body tissue 21. As illustrated in FIG. 6, after the collapsed retractor body 2 is positioned in place between the first body tissue 20 and the second body tissue 21, the retractor sections 3 are pivoted outwardly on the hinge 12 to extend the retractor body 2 from the collapsed configuration back to the expanded configuration such as by applying outward finger pressure against the finger grips 16. This action spreads the first body tissue 20 and the second body tissue 21 away from each other and, as illustrated in FIG. 6, enlarges the size of the surgical field 22, which communicates with the retractor interior 9. As illustrated in FIG. 7, surgical instruments 23 may then be inserted into the surgical field 22 through the retractor interior 9 to implement surgical procedures in the surgical field 22. It will be appreciated by those skilled in the art that the transparency of the retractor sections 3 of the retractor body 2 facilitates substantially unobstructed viewing of the surgical instruments 23 through the retractor sections 3 of the retractor body 2 during the surgical procedure. Upon conclusion of the surgical procedure, the surgical retractor 1 may be returned to the collapsed configuration, such as by applying inward pressure against the finger grips 16, and then removed from between the first body tissue 20 and the second body tissue 21.

Figure 8:
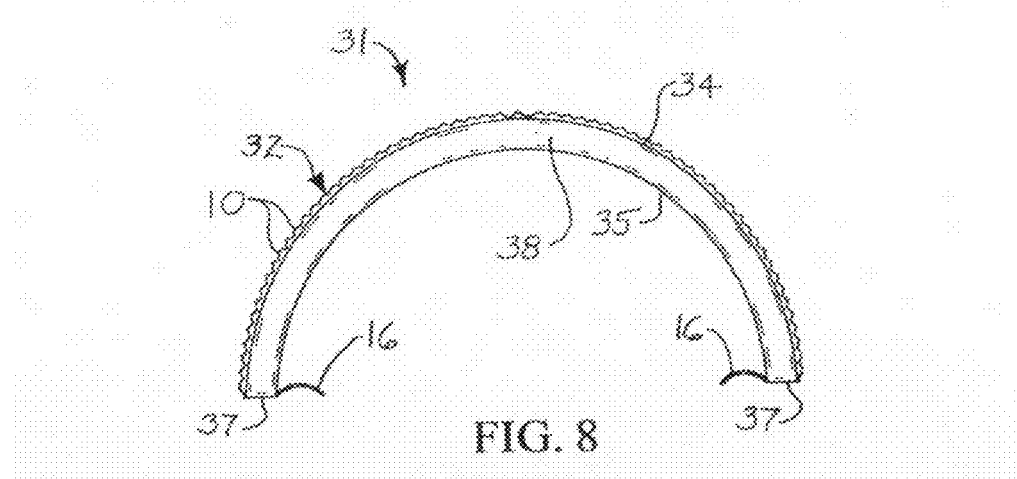
FIG. 8 is an end view of an alternative illustrative embodiment of the transparent surgical pelvic retractor, disposed in an expanded configuration.
Figure 9:
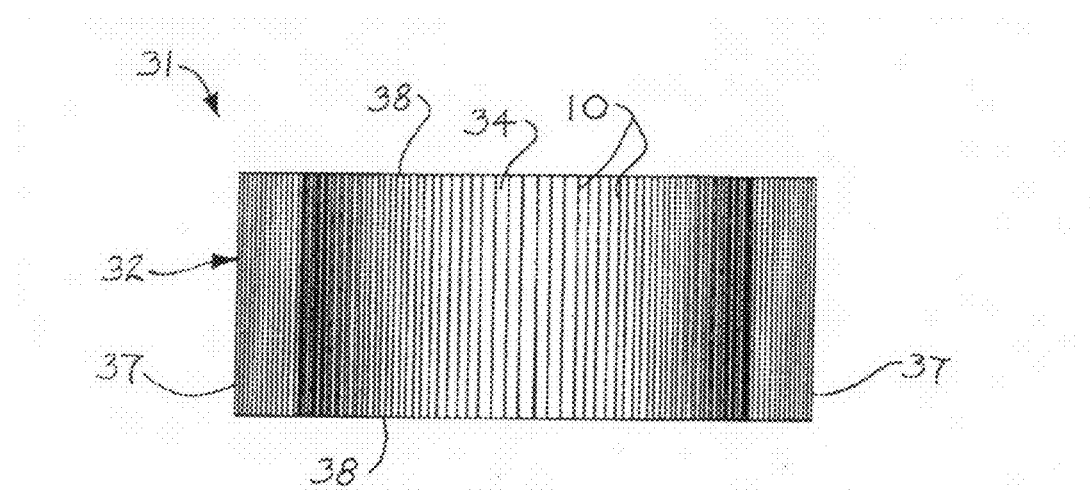
FIG. 9 is a top view of the illustrative embodiment of the transparent surgical pelvic retractor illustrated in FIG. 8.
Figure 10:
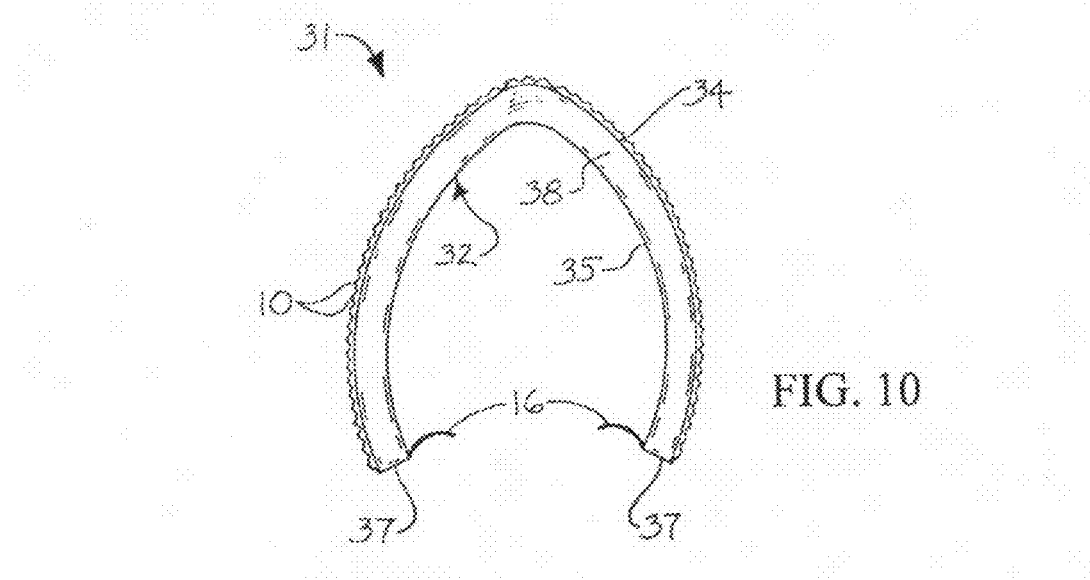
FIG. 10 is an end view of the illustrative embodiment of the transparent surgical pelvic retractor illustrated in FIG. 8, disposed in a flexed or collapsed configuration.

Referring next to FIGS. 8-10 of the drawings, an alternative illustrative embodiment of the transparent surgical pelvic retractor is generally indicated by reference numeral 31. The retractor 31 may include a generally semicircular retractor body 32 which may be a transparent, flexible plastic material and may be continuous and non-segmented. The retractor body 32 may have a convex outer body surface 34 and a concave inner body surface 35, with opposite lateral edges 37 and opposite end edges 38 which extend between and in generally perpendicular relationship with respect to the lateral edges 37, as illustrated in FIG. 9. In some embodiments, grip ridges 10 may be provided on the outer body surface 34 of the retractor body 32. The retractor body 32 can be selectively flexed from the expanded configuration illustrated in FIGS. 8 and 9 to the collapsed configuration illustrated in FIG. 10 by applying inward pressure against the finger grips 16. The retractor body 32 recoils back to the expanded configuration upon release of the finger grips 16 due to the flexibility of the retractor body 32.

Figure 11:
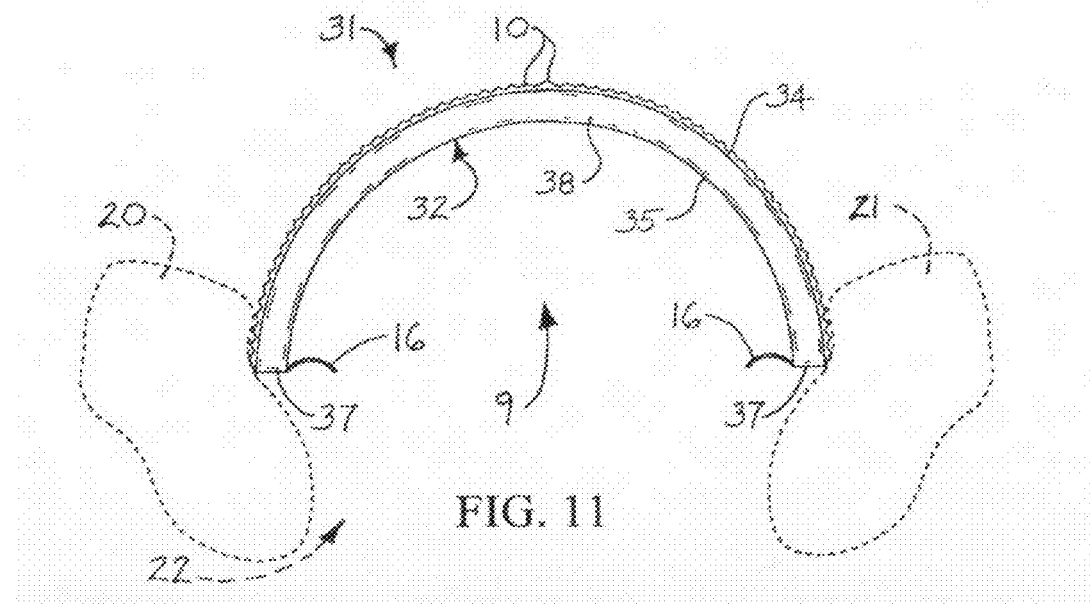
FIG. 11 is an end view of the illustrative embodiment of the transparent surgical pelvic retractor illustrated in FIG. 8, recoiled to the expanded configuration between body tissues (shown in phantom) to enlarge a surgical field between the tissues.

Typical use of the retractor 31 may be as was heretofore described with respect to the retractor 1 in FIGS. 4-7. Accordingly, the retractor 31 is flexed from the expanded configuration of FIGS. 8 and 9 to the collapsed configuration of FIG. 10 typically as inward finger pressure is applied to the finger grips 16 as the grip ridges 10 are gripped with the other hand. As it is inserted into position between the first body tissue 20 and the second body tissue 21 in the surgical patient, the retractor 31 is held in the collapsed configuration to facilitate clearance of the retractor 31 between the first body tissue 20 and the second body tissue 21. When the retractor 31 is placed into position between the first body tissue 20 and the second body tissue 21, the finger grips 16 are released. This causes the retractor 31 to recoil outwardly back to the expanded position and retract the first body tissue 20 and the second body tissue 21 away from each other to enlarge the surgical field 22, as illustrated in FIG. 11. A surgical procedure can then be carried out by inserting surgical instruments 23 (FIG. 7) into the surgical field 22 through the retractor interior 9 of the retractor 31. As was heretofore described with respect to FIG. 7, the transparency of the retractor body 32 facilitates substantially unobstructed viewing of the surgical instrument or instruments 23 through the retractor section 33 of the retractor body 32 during the surgical procedure. Upon conclusion of the surgical procedure, the surgical retractor 31 may be returned to the collapsed configuration, typically by applying inward pressure against the finger grips 16, and then removed from between the first body tissue 20 and the second body tissue 21.

Figure 12:
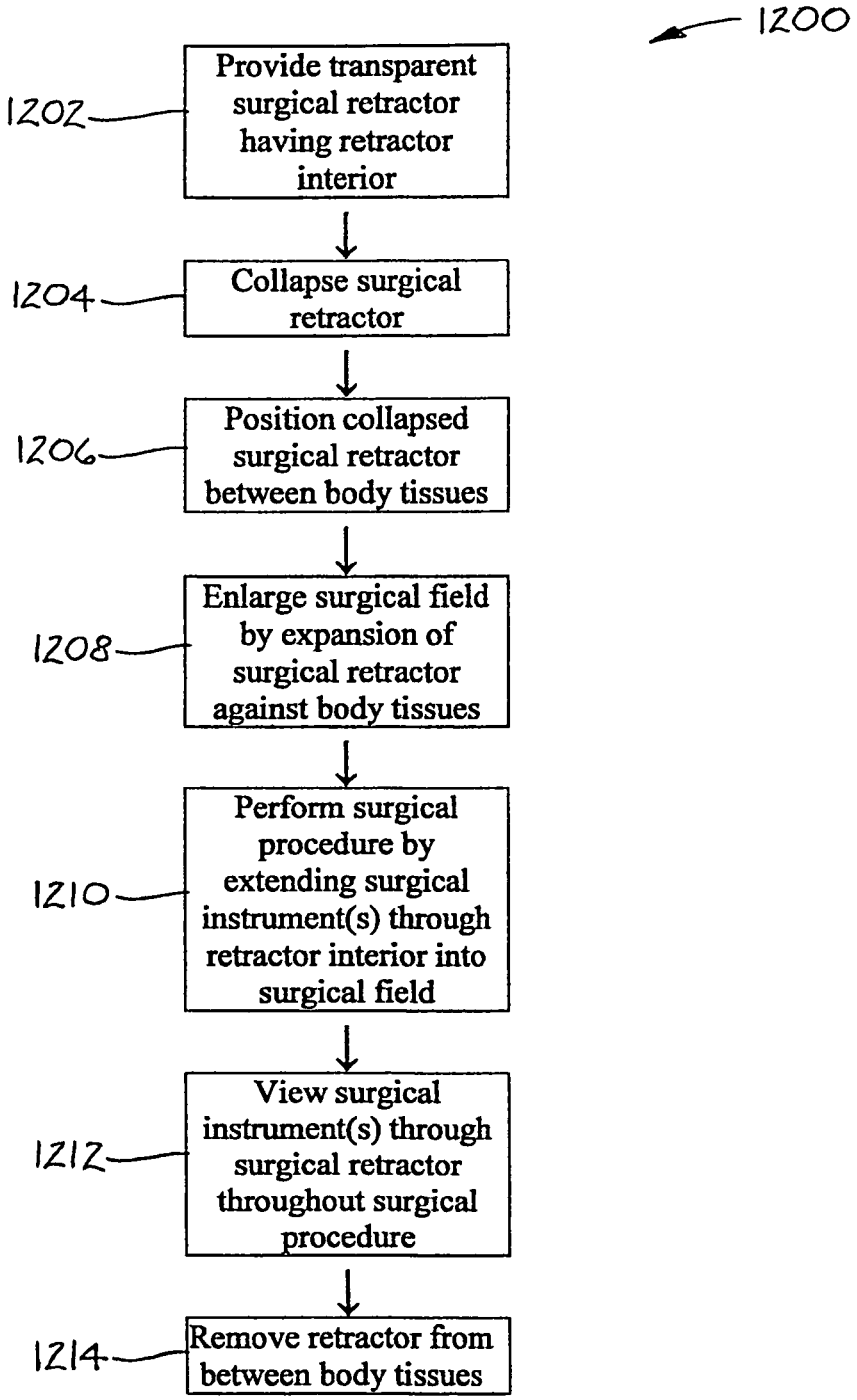
FIG. 12 is a flow diagram of an illustrative embodiment of a surgical retractor method.

Referring next to FIG. 12, a flow diagram 1200 of an illustrative embodiment of a surgical retractor method is illustrated. In block 1202, a transparent surgical pelvic retractor having a retractor interior is provided. In block 1204, the surgical retractor is collapsed. In block 1206, the collapsed surgical retractor is positioned between body tissues of a patient preparatory to an open surgical procedure. In block 1208, the surgical field is enlarged by expansion of the collapsed surgical retractor against the body tissues. In block 1210, a surgical procedure is performed by extending one or more surgical instruments through the retractor interior into the surgical field. In block 1212, the surgical instrument or instruments is/are viewed through the surgical retractor throughout the surgical procedure. In block 1214, the retractor is removed from between the body tissues at the conclusion of the surgical procedure.

Figure 13:
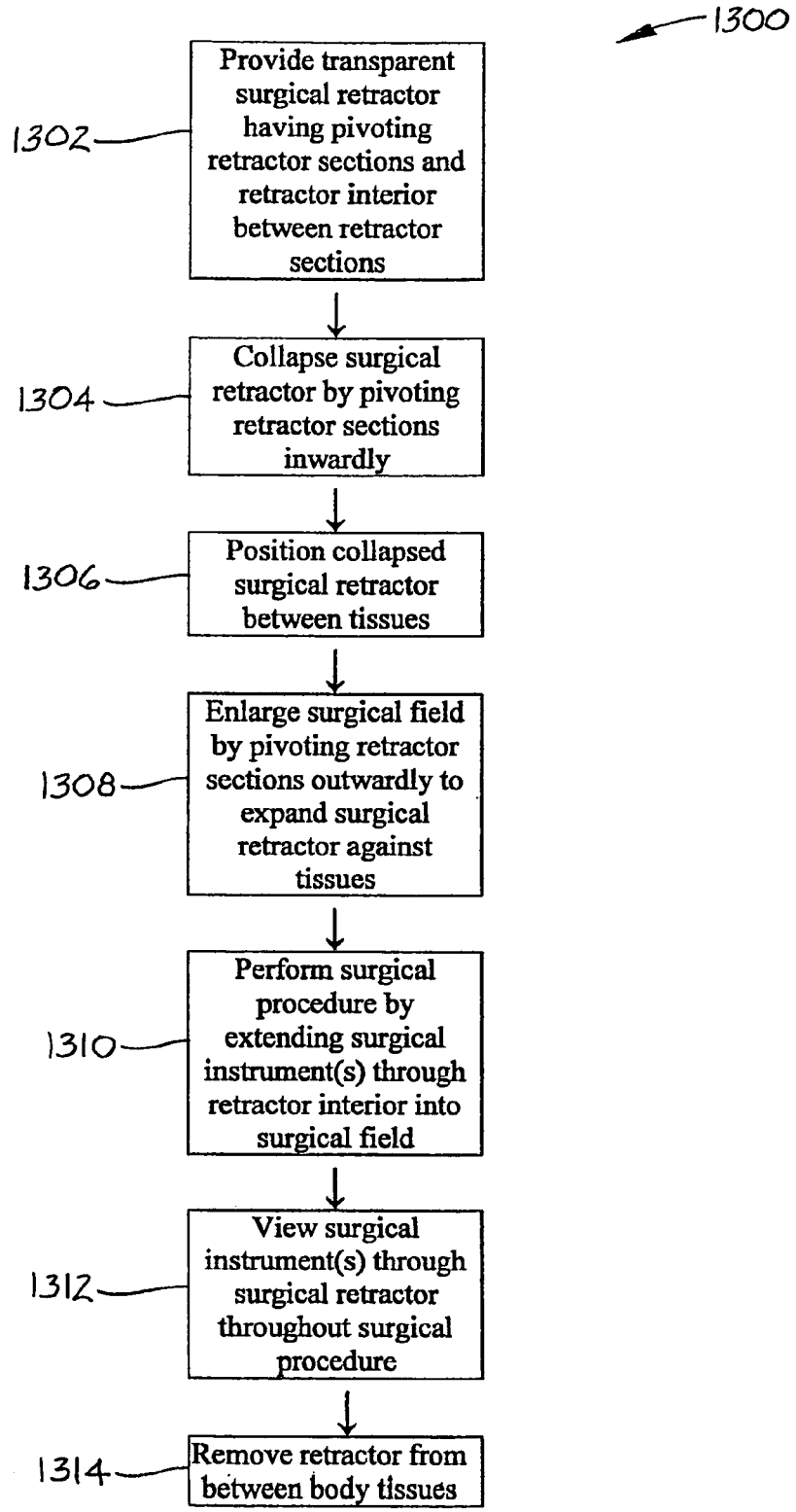
FIG. 13 is a flow diagram of an illustrative embodiment of a surgical retractor method which utilizes a surgical retractor having pivoting retractor sections.

Referring next to FIG. 13, a flow diagram 1300 of an illustrative embodiment of a surgical retractor method which utilizes a surgical retractor having pivoting retractor sections is illustrated. In block 1302, a transparent surgical pelvic retractor having pivoting retractor sections and a retractor interior between the retractor sections is provided. In block 1304, the surgical retractor is collapsed by pivoting the retractor sections inwardly. In block 1306, the collapsed surgical retractor is positioned between body tissues of a patient preparatory to an open surgical procedure. In block 1308, the surgical field is enlarged by pivoting the retractor sections outwardly to expand the surgical retractor against the tissues. In block 1310, an open surgical procedure is performed by extending a surgical instrument or instruments through the retractor interior into the surgical field. In block 1312, the surgical instrument or instruments is/are viewed through the surgical retractor throughout the surgical procedure. In block 1314, the retractor is removed from between the body tissues at the conclusion of the surgical procedure.

Figure 14:
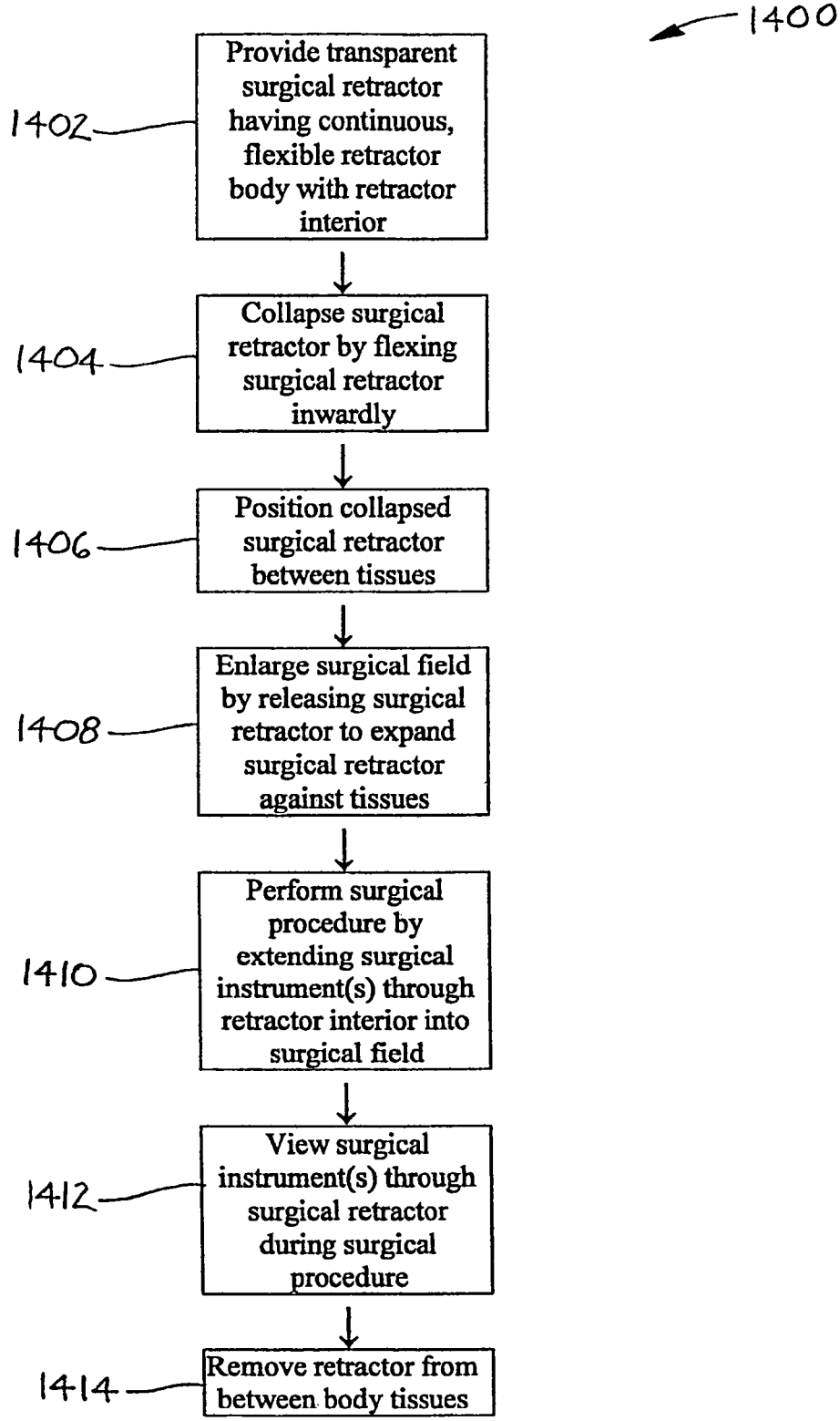
FIG. 14 is a flow diagram of an illustrative embodiment of a surgical retractor method which utilizes a surgical retractor having a continuous, flexible, transparent retractor body.

Referring next to FIG. 14, a flow diagram 1400 of an illustrative embodiment of a surgical retractor method which utilizes a surgical retractor having a continuous, flexible, transparent retractor body is illustrated. In block 1402, a transparent surgical pelvic retractor having a continuous, flexible retractor body with a retractor interior is provided. In block 1404, the surgical retractor is collapsed by flexing the retractor inwardly. In block 1406, the collapsed surgical retractor is positioned between body tissues in an open surgical procedure. In block 1408, the surgical field is enlarged by releasing and expanding the surgical retractor outwardly against the tissues. In block 1410, an open surgical procedure is performed by extending a surgical instrument or instruments through the retractor interior into the surgical field. In block 1412, the surgical instrument or instruments is/are viewed through the surgical retractor throughout the surgical procedure. In block 1414, the retractor is removed from between the body tissues at the conclusion of the surgical procedure.

Referring next to FIG. 15, another alternative illustrative embodiment of the transparent pelvic surgical retractor is generally indicated by reference numeral 41. The retractor 41 may be similar in design to the retractor 1 which was heretofore described with respect to FIGS. 1-3, except the retractor body 2 of the retractor 41 may include lateral edges 7 which taper toward each other from a first end edge 8 to a second end edge 11 of each retractor section 3. The tapered lateral edges 7 may provide a congruent fit of the retractor body 2 in the pelvic region of a surgical patient as the retractor 41 retracts the first tissue 20 and the second tissue 21 away from each other, as was heretofore described with respect to FIGS. 4-7.

Referring next to FIG. 16, still another alternative illustrative embodiment of the transparent pelvic surgical retractor is generally indicated by reference numeral 51. The retractor 51 may be similar in design to the retractor 41 which was heretofore described with respect to FIG. 15 except the outer section surface 4 of each retractor section 3 may lack the grip ridges 10. Multiple retractor body openings 52 may extend through each retractor section 3 in a selected pattern. Accordingly, the retractor body openings 52 may facilitate manual gripping of the retractor sections 3 as the retractor 51 is placed between the first tissue 20 and the second tissue 21.

Figure 17:
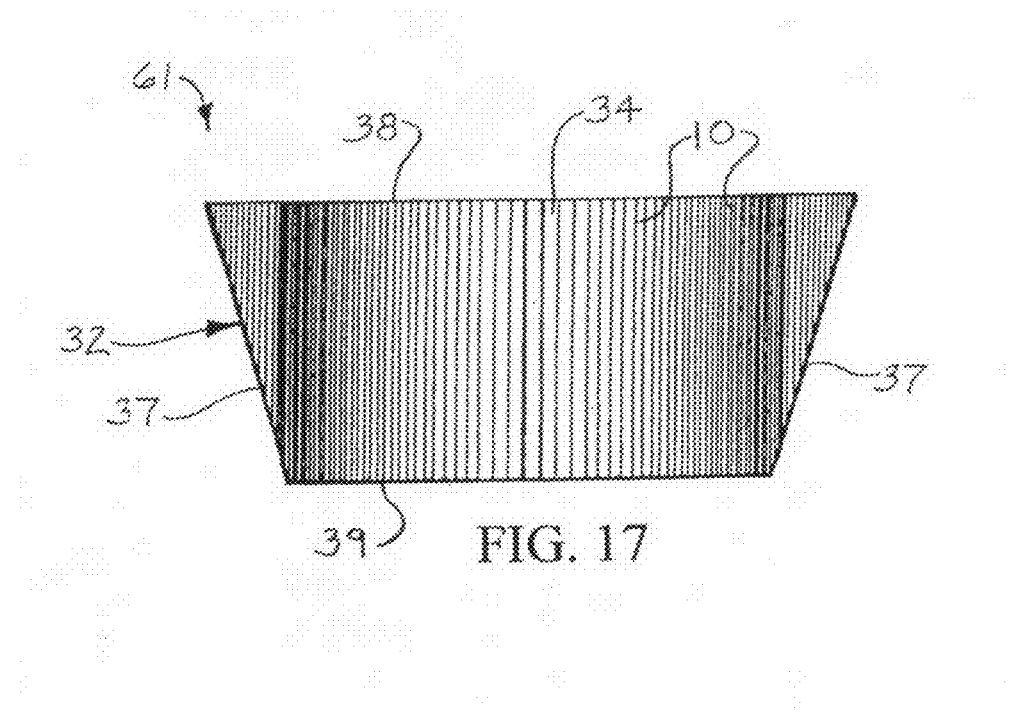
FIG. 17 is a top view of still another alternative illustrative embodiment of the transparent surgical pelvic retractor.

Referring next to FIG. 17, another alternative illustrative embodiment of the transparent pelvic surgical retractor is generally indicated by reference numeral 61. The retractor 1 may be similar in design to the retractor 31 which was heretofore described with respect to FIGS. 9 and 10 except the lateral edges 7 of the retractor body 32 may taper from a first end edge 38 to a second end edge 39 of the retractor body 32. The tapered lateral edges 7 may provide a congruent fit of the retractor body 2 in the pelvic region of a surgical patient as the retractor 41 retracts the first tissue 20 and the second tissue 21 away from each other, as was heretofore described with respect to FIGS. 4-7.

Figure 18:
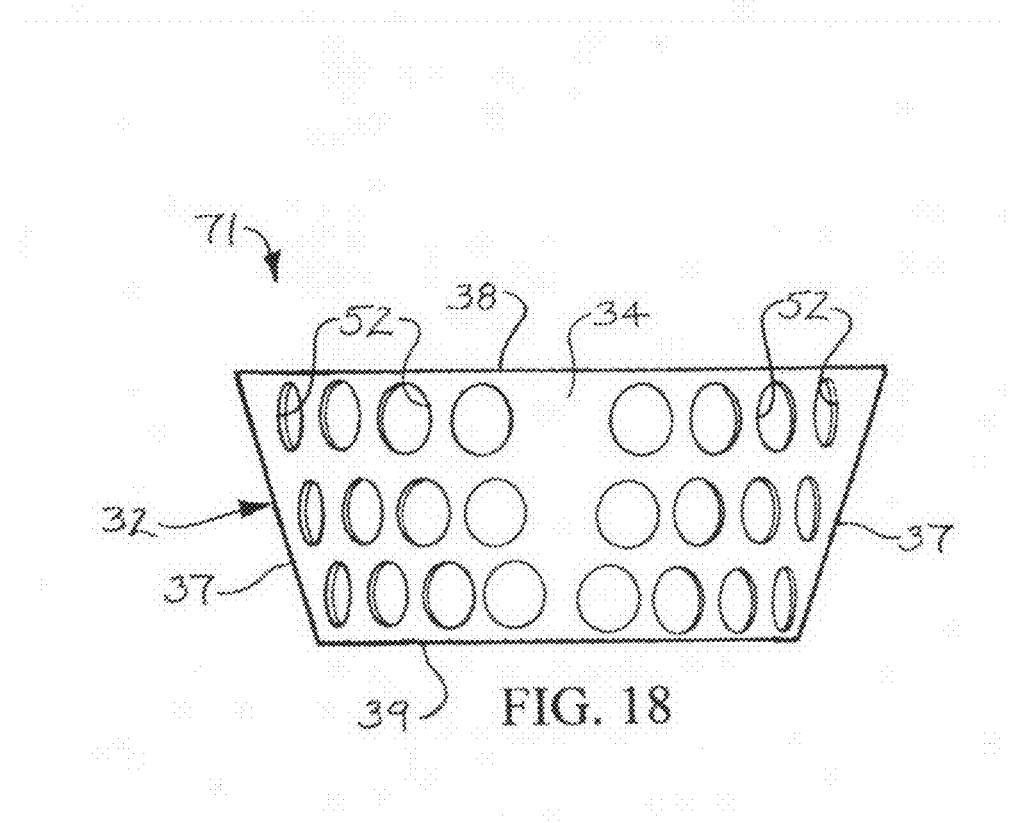
FIG. 18 is a top view of yet another alternative illustrative embodiment of the transparent surgical pelvic retractor.

Referring next to FIG. 18, yet another illustrative embodiment of the transparent pelvic surgical retractor is generally indicated by reference numeral 71. The retractor 71 may be similar in design to the retractor 61 which was heretofore described with respect to FIG. 17 except the outer section surface 34 of the retractor body 32 may lack the grip ridges 10. Multiple retractor body openings 52 may extend through the retractor body 32 in a selected pattern. Accordingly, the retractor body openings 52 may facilitate manual gripping of the retractor body 32 as the retractor 71 is placed between the first tissue 20 and the second tissue 21.

While the illustrative embodiments of the disclosure have been described above, it will be recognized and understood that various modifications can be made in the disclosure and the appended claims are intended to cover all such modifications which may fall within the spirit and scope of the disclosure.

What is claimed is:
1. A transparent surgical pelvic retractor, comprising:
a transparent, generally semicircular retractor body having a pail of retractor sections pivotally attached to each other, each of said retractor sections including a pair of elongated, parallel, spaced-apart end edges and a lateral edge and a medial edge extending between said end edges in spaced-apart, parallel relationship to each other and in perpendicular relationship to said end edges; a retractor interior formed by and between said retractor sections; a concave inner surface facing said retractor interior; a convex outer surface opposite said inner surface; and a plurality of elongated, parallel, spaced-apart grip ridges in said convex outer surface and extending in parallel relationship to said lateral edge and said medial edge and between and in perpendicular relationship to said end edges, said retractor body positional between expanded and collapsed positions with said retractor sections together forming a single semicircular shape in end view in said expanded position.

2. The transparent surgical pelvic retractor of claim 1 wherein said medial edge of a first of said pair of retractor sections is pivotally attached to a medial edge of a second one of said pair of retractor sections.

3. The transparent surgical pelvic retractor of claim 1 wherein said retractor body comprises a continuous and non-segmented retractor body.

4. A transparent surgical pelvic retractor, comprising:
a transparent, generally semicircular retractor body having a pair of retractor sections pivotally attached to each other, each of said retractor sections including a pair of elongated, parallel, spaced-apart end edges and a lateral edge tapering between said end edges and a medial edge extending between said end edges in perpendicular relationship to said end edges; a retractor interior formed by and between said retractor sections; a concave inner surface facing said retractor interior; a convex outer surface opposite said inner surface; and a plurality of elongated, parallel, spaced-part grip ridges in said convex outer surface and extending in parallel relationship to said medial edge and between and in perpendicular relationship to said end edges, said retractor body positional between expanded and collapsed positions with said retractor sections together forming a single semicircular shape in end view in said expanded position.

5. The transparent surgical pelvic retractor of claim 4 wherein said medial edge of a first of said pair of retractor sections is pivotally attached to a medial edge of a second one of said pair of retractor sections.

6. The transparent surgical pelvic retractor of claim 4 wherein said retractor body comprises a continuous and non-segmented retractor body.

7. A transparent surgical pelvic retractor, comprising:
a transparent, generally semicircular retractor body having a pair of retractor sections pivotally attached to each other, each of said retractor sections including a pair of elongated, parallel, spaced-apart end edges and a lateral edge tapering between said end edges and a medial edge extending between said end edge; in perpendicular relationship to said end edges; a retractor interior formed by and between said retractor sections; a concave inner surface facing said retractor interior; a convex outer surface opposite said inner surface; and a plurality of retractor body openings extending through each of said retractor sections, said retractor body positional between expanded and collapsed positions with said retractor sections together forming a single semicircular shape in end view in said expanded position.

8. The transparent surgical pelvic retractor of claim 7 wherein said medial edge of a first of said pair of retractor sections is pivotally attached to a medial edge of a second one of said pair of retractor sections.

9. The transparent surgical pelvic retractor of claim 7 wherein said retractor body comprises a continuous and non-segmented retractor body.

\* \* \* \* \*